US009382585B2

(12) United States Patent
Oliphant

(10) Patent No.: US 9,382,585 B2
(45) Date of Patent: Jul. 5, 2016

(54) APPARATUS FOR HIGH THROUGHPUT SEQUENCING OF NUCLEIC ACIDS

(75) Inventor: Arnold Oliphant, Sunnyvale, CA (US)

(73) Assignee: Complete Genomics, Inc., Mountain View, CA (US)

(*) Notice: Subject to any disclaimer, the term of this patent is extended or adjusted under 35 U.S.C. 154(b) by 678 days.

(21) Appl. No.: 12/261,548

(22) Filed: Oct. 30, 2008

(65) Prior Publication Data

US 2009/0155793 A1 Jun. 18, 2009

Related U.S. Application Data

(60) Provisional application No. 60/983,886, filed on Oct. 30, 2007.

(51) Int. Cl.
C12Q 1/68 (2006.01)
G01N 35/00 (2006.01)
G01N 21/64 (2006.01)

(52) U.S. Cl.
CPC .......... C12Q 1/6874 (2013.01); G01N 21/6486 (2013.01); G01N 35/0099 (2013.01); G01N 2035/00158 (2013.01); G01N 2201/0461 (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,883,750 A | 11/1989 | Whiteley et al. |
| 4,965,188 A | 10/1990 | Mullis et al. |
| 5,091,652 A | 2/1992 | Mathies et al. |
| 5,210,015 A | 5/1993 | Gelfand et al. |
| 5,395,502 A | 3/1995 | Pawliszyn |
| 5,399,491 A | 3/1995 | Kacian et al. |
| 5,426,180 A | 6/1995 | Kool |
| 5,445,934 A | 8/1995 | Fodor et al. |
| 5,476,930 A | 12/1995 | Letsinger et al. |
| 5,593,826 A | 1/1997 | Fung et al. |
| 5,854,033 A | 12/1998 | Lizardi |
| 5,871,921 A | 2/1999 | Landegren |
| 5,958,760 A | 9/1999 | Freeman |
| 6,008,892 A | 12/1999 | Kain et al. |

(Continued)

FOREIGN PATENT DOCUMENTS

| | | |
|---|---|---|
| EP | 0962772 A2 | 12/1999 |
| JP | 2003294757 A2 | 10/2003 |

(Continued)

OTHER PUBLICATIONS

International Search Report PCT/US08/81818 dated Jan. 16, 2009.

(Continued)

Primary Examiner — Robert T Crow
(74) Attorney, Agent, or Firm — Kenneth R. Allen; Michael Schiff; Kilpatrick Townsend & Stockton LLP

(57) ABSTRACT

A scalable reaction and detection system for automated high throughput sequencing of nucleic acids involving a combination of chemical processes and observation processes independent of the chemistry processes. Discrete functional units may be configured in a manner that allows the system to interchangeably utilize different sequencing reaction components in conjunction with discrete apparatus components for optical image collection and/or analysis.

21 Claims, 4 Drawing Sheets

(56) References Cited

U.S. PATENT DOCUMENTS

| | | | |
|---|---|---|---|
| 6,174,670 B1 | 1/2001 | Wittwer et al. | |
| 6,177,990 B1 | 1/2001 | Kain et al. | |
| 6,210,891 B1 | 4/2001 | Nyren et al. | |
| 6,287,824 B1 | 9/2001 | Lizardi | |
| 6,289,144 B1 | 9/2001 | Neuschafer et al. | |
| 6,306,597 B1 | 10/2001 | Macevicz | |
| 6,309,824 B1 | 10/2001 | Drmanac | |
| 6,396,995 B1 | 5/2002 | Stuelpnagal et al. | |
| 6,401,267 B1 | 6/2002 | Drmanac | |
| 6,403,376 B1 | 6/2002 | Toner et al. | |
| 6,455,260 B1 | 9/2002 | Muller et al. | |
| 6,544,732 B1 | 4/2003 | Chee et al. | |
| 6,632,605 B1* | 10/2003 | Cronin et al. | 435/6 |
| 6,833,246 B2 | 12/2004 | Balasubramanian | |
| 6,864,052 B1 | 3/2005 | Drmanac et al. | |
| 6,911,345 B2 | 6/2005 | Quake et al. | |
| 6,960,437 B2 | 11/2005 | Enzelberger et al. | |
| 7,010,964 B2 | 3/2006 | Karp et al. | |
| 7,025,935 B2 | 4/2006 | Jones et al. | |
| 7,070,927 B2 | 7/2006 | Drmanac | |
| 7,118,910 B2 | 10/2006 | Unger et al. | |
| 7,198,901 B1 | 4/2007 | Rachlin | |
| 7,220,549 B2 | 5/2007 | Buzby | |
| 7,238,323 B2 | 7/2007 | Knapp et al. | |
| 7,244,559 B2 | 7/2007 | Rothberg et al. | |
| 7,264,929 B2 | 9/2007 | Rothberg et al. | |
| 7,270,784 B2 | 9/2007 | Vuong et al. | |
| 7,897,344 B2 | 3/2011 | Dahl et al. | |
| 7,901,890 B2 | 3/2011 | Dahl et al. | |
| 7,910,302 B2 | 3/2011 | Drmanac et al. | |
| 7,910,354 B2 | 3/2011 | Drmanac et al. | |
| 7,960,104 B2 | 6/2011 | Drmanac et al. | |
| 8,133,719 B2 | 3/2012 | Drmanac et al. | |
| 8,175,452 B1 | 5/2012 | Staker et al. | |
| 8,415,099 B2 | 4/2013 | Drmanac et al. | |
| 8,428,454 B2 | 4/2013 | Staker et al. | |
| 8,440,397 B2 | 5/2013 | Drmanac et al. | |
| 8,445,194 B2 | 5/2013 | Drmanac et al. | |
| 8,445,196 B2 | 5/2013 | Drmanac et al. | |
| 8,445,197 B2 | 5/2013 | Drmanac et al. | |
| 8,518,640 B2 | 8/2013 | Drmanac et al. | |
| 8,551,702 B2 | 10/2013 | Drmanac et al. | |
| 8,609,335 B2 | 12/2013 | Drmanac et al. | |
| 8,615,365 B2 | 12/2013 | Halpern et al. | |
| 8,660,421 B2 | 2/2014 | Staker et al. | |
| 8,722,326 B2 | 5/2014 | Drmanac et al. | |
| 8,731,843 B2 | 5/2014 | Halpern et al. | |
| 8,738,296 B2 | 5/2014 | Halpern et al. | |
| 8,774,494 B2 | 7/2014 | Staker | |
| 2001/0005489 A1* | 6/2001 | Roach et al. | 422/99 |
| 2002/0182117 A1* | 12/2002 | Coassin et al. | 422/100 |
| 2003/0032191 A1* | 2/2003 | Hilson et al. | 436/47 |
| 2003/0152485 A1* | 8/2003 | Trutnau et al. | 422/81 |
| 2004/0033166 A1* | 2/2004 | Arnowitz et al. | 422/82.05 |
| 2004/0110213 A1 | 6/2004 | Namsaraev | |
| 2004/0259111 A1 | 12/2004 | Marlowe et al. | |
| 2005/0161669 A1* | 7/2005 | Jovanovich et al. | 257/48 |
| 2005/0191656 A1 | 9/2005 | Drmanac et al. | |
| 2006/0024711 A1 | 2/2006 | Lapidus et al. | |
| 2006/0078895 A1* | 4/2006 | Peck et al. | 435/6 |
| 2006/0260941 A1* | 11/2006 | Tan et al. | 204/450 |
| 2007/0087362 A1 | 4/2007 | Church et al. | |
| 2007/0128610 A1 | 6/2007 | Buzby | |
| 2007/0207482 A1 | 9/2007 | Church et al. | |
| 2009/0155793 A1* | 6/2009 | Oliphant | 435/6 |
| 2011/0004413 A1 | 1/2011 | Carnevali et al. | |
| 2012/0224050 A1 | 9/2012 | Staker | |
| 2014/0152793 A1 | 6/2014 | Staker et al. | |
| 2014/0152888 A1 | 6/2014 | Staker et al. | |

FOREIGN PATENT DOCUMENTS

| | | | |
|---|---|---|---|
| WO | 94/08759 A1 | 4/1994 | |
| WO | 01/35088 A1 | 5/2001 | |
| WO | WO 01/35088 A1 | 5/2001 | |
| WO | 01/68257 A1 | 9/2001 | |
| WO | 2004/076683 A2 | 9/2004 | |
| WO | 2004/108270 A2 | 12/2004 | |
| WO | 2005/082098 A2 | 9/2005 | |
| WO | WO 2005/082098 A2 | 9/2005 | |
| WO | WO 2005/093388 A1 * | 10/2005 | G01N 1/28 |
| WO | 2006/073504 A2 | 7/2006 | |
| WO | 2006/074351 A2 | 7/2006 | |
| WO | WO 2006/073504 A2 | 7/2006 | |
| WO | 2006/084132 A2 | 8/2006 | |
| WO | 2006/124842 A2 | 11/2006 | |
| WO | 2009/059022 A1 | 5/2009 | |

OTHER PUBLICATIONS

Allawi et al., "Thermodynamics and NMR of Internal G-T Mismatches in DNA," © 1997 American Chemical Society, Biochemistry 1997, 36, pp. 10581-10594.

Xu et al., "High sequence fidelity in a non-enzymatic DNA autoligation reaction," © 1999 Oxford University Press, Nucleic Acids Research, 1999, vol. 27, No. 3, pp. 875-881.

European Search Report for European Application No. 08844709.9 mailed on Jul. 31, 2012, 7 pages.

Communication pursuant to Article 94(3) EPC of Mar. 26, 2015 for European Application No. 08844709.9, 8 pages.

Drmanac et al., "Human genome sequencing using unchained base reads on self-assembling DNA nanoarrays", Science, Jan. 2010, 327, pp. 78-81.

\* cited by examiner

APPARATUS FOR HIGH THROUGHPUT SEQUENCING OF NUCLEIC ACIDS

CROSS-REFERENCES TO RELATED APPLICATIONS

The present application claims benefit under 35 USC 119 (e) of U.S. provisional Application No. 60/983,886, filed on Oct. 30, 2007 entitled "Apparatus For High Throughput Sequencing Of Nucleic Acids," the content of which is incorporated herein by reference in its entirety.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The invention relates generally to the field of automated optical detection of nucleic acids. The present invention is directed, in general, to scalable reaction and detection systems for automated high throughput sequencing of nucleic acids.

The advent of the human genome project required that improved methods for sequencing nucleic acids, such as DNA (deoxyribonucleic acid) and RNA (ribonucleic acid), be developed. Determination of the entire 3,000,000,000 base sequence of the human genome has provided a foundation for identifying the genetic basis of numerous diseases. However, a great deal of work remains to be done to identify the genetic variations associated with each disease, and the current cost of sequencing 6,000,000,000 bases for each individual (the size of the diploid human genome) remains not only exceedingly difficult, but also cost-prohibitive.

Numerous companies have approached the challenge of high throughput DNA sequencing with the development of DNA sequencing systems. Although such systems have decreased the cost and increased the efficiency of DNA sequencing, these systems are generally self-contained units with multiple interdependent components. Such single unit sequencing systems have numerous limitations, including limited scalability, a time lag in the introduction of innovations to specific components, and direct dependency of function of the entire system on each component of the system.

Flow cells for sequencing reaction and analysis are known. Examples of such flow cells include those comprising any substrate used for the performance of a sequencing reaction, such as those described in more detail herein, as well as those described in U.S. Pat. Nos. 5,958,760, 6,403,376, 6,960,437, 7,025,935, 7,118,910, 7,220,549, 7,244,559, 7,264,929, WO 01/35088, and Published U.S. Patent App. 2007/0128610.

The current invention addresses limitations of known prior art.

DEFINITIONS

In order to have a sufficient background in the present technology, it is helpful to understand the following terms of art.

"Amplicon" means the product of a polynucleotide amplification reaction, namely, a population of polynucleotides that are replicated from one or more starting sequences. Amplicons may be produced by a variety of amplification reactions, including but not limited to polymerase chain reactions (PCRs), linear polymerase reactions, nucleic acid sequence-based amplification, rolling circle amplification and like reactions (see, e.g., U.S. Pat. Nos. 4,683,195; 4,965,188; 4,683,202; 4,800,159; 5,210,015; 6,174,670; 5,399,491; 6,287,824 and 5,854,033; and US Pub. No. 2006/0024711).

"Array" or "microarray" refers to a solid support having a surface, preferably but not exclusively a planar or substantially planar surface, which carries a collection of sites comprising nucleic acids such that each site of the collection is spatially defined and not overlapping with other sites of the array; that is, the sites are spatially discrete. The array or microarray can also comprise a non-planar interrogatable structure with a surface such as a bead or a well. The oligonucleotides or polynucleotides of the array may be covalently bound to the solid support, or it may be non-covalently bound. Conventional microarray technology is reviewed in, e.g., Schena, Ed. (2000), *Microarrays: A Practical Approach* (IRL Press, Oxford). As used herein, "random array" or "random microarray" refers to a microarray where the identity of the oligonucleotides or polynucleotides is not discernable, at least initially, from their location but may be determined by a particular biochemistry detection technique on the array. See, e.g., U.S. Pat. Nos. 6,396,995; 6,544,732; 6,401,267; and 7,070,927; WO publications WO 2006/073504 and 2005/082098; and US Pub Nos. 2007/0207482 and 2007/0087362.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1M, more usually less than about 500 mM and less than about 200 mM. A "hybridization buffer" is a buffered salt solution such as 5× SSPE, or the like. Hybridization temperatures can be as low as 5° C., but are typically greater than 22° C., more typically greater than about 30° C., and preferably in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5× SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning: A laboratory Manual" $2^{nd}$ Ed. Cold Spring Harbor Press (1989) and Anderson "Nucleic Acid Hybridization" $1^{st}$ Ed., BIOS Scientific Publishers Limited (1999).

"Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with a 3' carbon of another oligonucleotide. A variety of template-driven ligation reactions are described in the following references: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213. Enzymatic ligation usually takes place in a ligase buffer, which is a buffered salt solution containing any required divalent cations, cofactors, and the like, for the particular ligase employed.

"Mismatch" means a base pair between any two of the bases A, T (or U for RNA), G, and C other than the Watson-Crick base pairs G-C and A-T. The eight possible mismatches are A-A, T-T, G-G, C-C, T-G, C-A, T-C, and A-G.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following process: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each reaction condition in a thermal cycler instrument. Particular temperatures, durations and rates of change between reactions depend on many factors well-known to those of ordinary skill in the art, e.g. exemplified by the references: McPherson et al., editors, *PCR: A Practical Approach* and *PCR2: A Practical Approach* (IRL Press, Oxford, 1991 and 1995, respectively). For example, in a conventional PCR using Taq DNA polymerase, a double-stranded target nucleic acid may be denatured at a temperature >90° C., primers annealed at a temperature in the range 50-75° C., and primers extended at a temperature in the range 72-78° C. As above, the term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g., 200 nL, to a few hundred µL, e.g., 200 µL.

"Nucleic acid" and "oligonucleotide" are used herein to mean a polymer of nucleotide monomers. As used herein, the terms may also refer to-double stranded forms. Monomers making up nucleic acids and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like, to form duplex or triplex forms. Such monomers and their internucleosidic linkages may be naturally occurring or may be analogs thereof, e.g., naturally occurring or non-naturally occurring analogs. Non-naturally occurring analogs may include peptide nucleic acids, locked nucleic acids, phosphorothioate internucleosidic linkages, bases containing linking groups permitting the attachment of labels, such as fluorophores, or haptens, and the like. Whenever the use of an oligonucleotide or nucleic acid requires enzymatic processing, such as extension by a polymerase, ligation by a ligase, or the like, one of ordinary skill would understand that oligonucleotides or nucleic acids in those instances would not contain certain analogs of internucleosidic linkages, sugar moieties, or bases at any or some positions, when such analogs are incompatible with enzymatic reactions. Nucleic acids typically range in size from a few monomeric units, e.g., 5-40, when they are usually referred to as "oligonucleotides," to several hundred thousand or more monomeric units. Whenever a nucleic acid or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, *Human Molecular Genetics* 2 (Wiley-Liss, New York, 1999). Usually nucleic acids comprise the natural nucleosides (e.g., deoxyadenosine, deoxycytidine, deoxyguanosine, deoxythymidine for DNA or their ribose counterparts for RNA) linked by phosphodiester linkages; however, they may also comprise non-natural nucleotide analogs, e.g., modified bases, sugars, or internucleosidic linkages. To those skilled in the art, where an enzyme has specific oligonucleotide or nucleic acid substrate requirements for activity, e.g., single-stranded DNA, RNA/DNA duplex, or the like, then selection of appropriate composition for the oligonucleotide or nucleic acid substrates is well within the knowledge of one of ordinary skill, especially with guidance from treatises, such as Sambrook et al., *Molecular Cloning*, Second Edition (Cold Spring Harbor Laboratory, New York, 1989), and like references.

"Primer" means an oligonucleotide, either natural or synthetic, which is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 9 to 40 nucleotides, or in some embodiments, from 14 to 36 nucleotides.

"Probe" as used herein refers to an oligonucleotide, either natural or synthetic, which is used to interrogate complementary sequences within a nucleic acid of unknown sequence. The hybridization of a specific probe to a target polynucleotide is indicative of the specific sequence complementary to the probe within the target polynucleotide sequence.

"Readout" means a parameter, or parameters, that are measured and/or detected and that can be expressed as a number, a value or other indicia for evaluation. In some contexts, readout may refer to an actual numerical representation of such collected or recorded data. For example, a readout of fluorescent intensity signals from a microarray is the position and fluorescence intensity of a signal being generated at each hybridization site of the microarray; thus, such a readout may be registered or stored in various ways, for example, as an image of the microarray, as a table of numbers, or the like.

"Solid support" and "support" are used interchangeably and refer to a material or group of materials having a rigid or semi-rigid surface or surfaces. Microarrays usually comprise at least one planar solid phase support, such as a glass microscope slide.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1M NaCl (see e.g., Anderson and Young, *Quantitative Filter Hybridization, in Nucleic Acid Hybridization* (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of $T_m$.

By way of explanation, unless defined otherwise, all technical and scientific terms used herein have the same meaning as commonly understood by one of ordinary skill in the art to which this invention belongs.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, and except where indicated, the molecular biology and sequencing analysis referred to with respect to the invention are, in their basic aspects, conventional methods within the skill of the art of those employed in the relevant field. Such techniques are explained fully in the literature, see, e.g., Maniatis, Fritsch & Sambrook, Molecular Cloning: A Laboratory Manual (1982); and Sambrook, Russell and Sambrook, Molecular Cloning: A Laboratory Manual (2001). Terms and symbols of nucleic acid chemistry, biochemistry, genetics, and molecular biology used herein follow those of standard treatises and texts in the field, e.g., Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

BRIEF SUMMARY OF THE INVENTION

According to the invention, a system for performing nucleic acid sequencing for genome analysis comprises discrete functional units, for example for sample preparation and for observation, that may be configured in a manner that allows interchangeable utilization of different sequencing reaction components with discrete apparatus components for optical image collection and/or analysis to minimize bottlenecks in sample preparation and data extraction that operate at different rates.

The present invention provides high-throughput systems for the sequence determination of nucleic acids of unknown sequence. Systems according to the invention comprise multiple, purpose-based, discrete components that are physically loosely-coupled within such system and reversibly integrated for sequence interrogation and analysis. The loosely coupled and reversible integrated nature of the system provides greater efficiency and versatility in the use of the various system components, allowing optimization of the system based on the time requirements and the capabilities of each component. This allows for improved scalability, ease of adding improvements to the system, and the creation of multiple system configurations with an enhanced user flexibility compared to fully integrated systems presently available in the art.

Having the system elements loosely coupled and reversibly integrated provides numerous benefits, including facilitating any repairs that need to be made in a single component of the system while not disrupting the other components overall system. In addition, the coupling strategy of the individual system components facilitates the introduction of any improvement to a single component, thus promoting the use of new innovations and providing the latest state of the art innovations to the overall system.

In specific embodiments of the invention, higher throughput can be achieved by using multiple components in the performance of the respective activities needed for nucleic acid sequencing. For example, using multiple optical detection instruments and/or multiple sequencing reaction components can greatly increase the number of sequences determined and decrease the time required for doing so.

In one of the embodiments, a single reaction apparatus for sequencing and a single optical detection and analysis instrument are provided, with the reaction apparatus being physically loosely coupled and reversibly integrated with the optical instrument.

In another embodiment, multiple biochemistry components and a single optical detection instrument are provided for use with different sequencing reaction components, e.g., components directed to sequencing by synthesis and components directed to sequencing by probe ligation. The sequencing reaction components of such systems can be kept in discrete units, with each unit reversibly interconnected physically to an optical imaging system. This allows a single system to utilize different sequencing technologies and benefit from the strengths of multiple different sequencing approaches in a single device configuration. The optical instrument can be disposed in a single system having an analysis component, or they may be deployed as two separate components of the overall system.

In one specific embodiment, the system may comprise three compartmentalized components: (i) a fluidics system for storing and transferring detection and processing reagents, e.g., probes, wash solutions, and the like; (ii) a reaction platform for carrying out the biochemical sequencing reactions in a series of reaction chambers, or flow cell(s); and (iii) a discrete illumination and detection system for capture of optical images of the sequencing reactions and analysis of such images.

The reaction platform for the biochemical sequencing reactions preferably has multiple reaction units comprising individual flow cells and a mechanism for transfer of each flow cell from the reaction apparatus to the illumination and detection system following completion of the biochemical sequencing reaction.

In a preferred aspect of multiple embodiments, the flow cells comprise an array of nucleic acids of unknown sequence attached to a solid surface, e.g., glass or a flexible material such as a film or membrane. In another embodiment, each flow cell comprises an array of nucleic acids of unknown sequence attached to beads which are optionally attached to a solid or semi-solid surface.

In a certain aspect of the embodiments of the invention, the sequencing reaction component of the system provides a plurality of flow cells for use in processing a sample. In a preferred aspect, each flow cell comprises a substantially sealed chamber with a fluid inlet and a fluid outlet for the introduction and removal respectively of fluids used in the sequencing reaction.

In a specific embodiment, two or more sequencing reaction platforms can be interconnected to a single optical imaging system, which can record and analyze the separate sequencing information from each reaction unit. In a specific aspect, each of the reaction units and flow cells on the multiple reaction platforms are designed to carry out the same high throughput nucleic acid sequencing biochemistry on a plurality of flow cells. In another aspect, the different reaction platforms and flow cells are designed to accommodate different biochemical approaches to high throughput nucleic acid sequencing, with each reaction platform optimized to carry out a specific flow cell sequencing reaction. The ability to have optimized reaction platforms and flow cell biochemical reaction units, each designed to accommodate the specific biochemistry of a sequencing approach, reversibly interconnected with a single illumination and analysis system provides optimum use of space and run time and is more cost effective than having separate complete systems for each potential biochemical sequencing application.

In a particular aspect of certain embodiments, part of the internal surface of each of the flow cells is defined by the sample-bearing surface of the support, which arrangement has the advantage of minimizing the number of components involved in the flow cell assembly.

In a specific embodiment, the flow cells of a specific sequencing reaction unit each comprise an array of target nucleic acids of unknown sequence by sandwiching the glass and a gasket between two solid planar surfaces. One plane has an opening of sufficient size to permit imaging, and an indexing pocket for the cover slip. The other plane has an indexing pocket for the gasket, fluid ports, and an optional temperature control system.

In one specific aspect of the invention, a flow cell designed for specific use with a sequencing reaction unit comprises a 1" square, 170 micrometer thick cover slip. In a preferred embodiment, this flow cell has one surface that has been derivatized to bind macromolecular biologic structures of unknown sequence for high throughput, genome-scale sequencing.

In certain specific aspects of the invention, the flow cells may comprise a fluid port connected to a device (e.g., a syringe pump) with the ability to effect exit or entry of fluid from the flow cell.

In another specific aspect of the invention, the flow cell comprises a port connected to a mixing chamber, which is optionally equipped with a liquid level sensor. Solutions needed for the sequencing reaction are dispensed into the chamber, mixed if needed, then drawn into the flow cell. In a preferred aspect, the chamber is conical in nature and acts as a funnel. In certain aspects of the embodiments of the invention, each flow cell comprises a temperature control subsystem with ability to maintain temperature in the range from about 5-95° C., or more specifically 10-85° C., and can change temperature with a rate of about 0.5-2° C. per second.

In a further aspect of certain embodiments of the invention, the system further provides an automated apparatus for processing a sample, especially a biological sample, supported on a support, the apparatus comprising: support holding means for holding one or more supports, the sample on the or each support being present within a respective substantially sealed chamber; fluid delivery means for delivering processing fluid to the or each chamber; waste fluid collecting means for removing fluid from the or each chamber; and computer control means for monitoring the sequencing reaction. Preferably the apparatus is used in conjunction with one or more of the flow cells defined above.

The invention will be better understood to those persons skilled in the art upon reading the details of the methods as more fully described below.

DETAILED DESCRIPTION OF THE INVENTION

Figure 1:
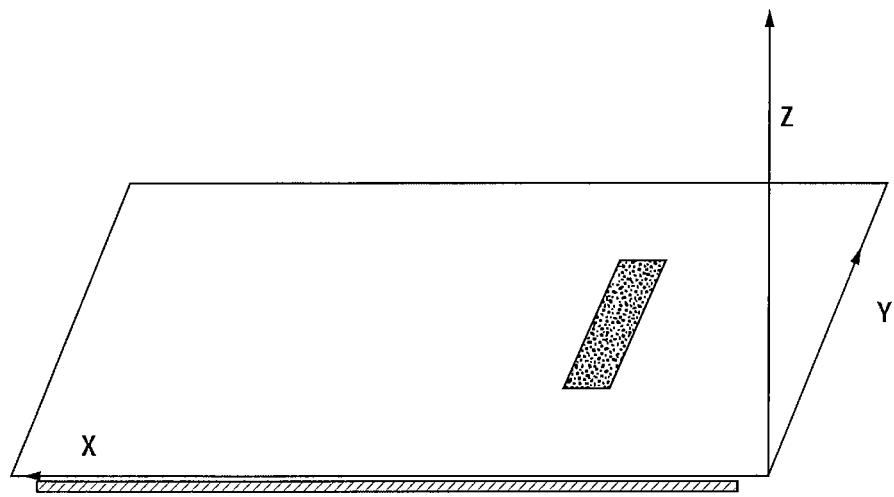
FIG. 1 is a graphic drawing illustrating the basic format of a sequencing reaction platform of the invention.

FIG. 1 shows a schematic side view of an exemplary sequencing reaction platform with a reaction workspace and having a lengthwise dimension X, a width dimension Y, and a height dimension Z.

Figure 2:
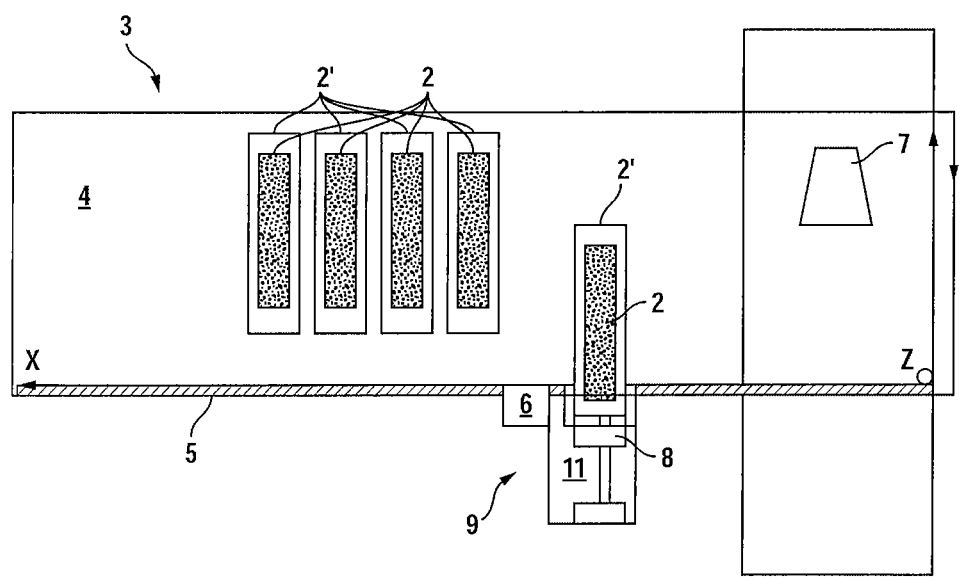
FIG. 2 is a graphic drawing illustrating a first embodiment of a system comprising a sequencing reaction platform and an optical imaging device.

FIG. 2 shows a schematic top view of a first sequencing reaction platform of one preferred aspect of the sequencing system embodiments of the invention. Platforms of this nature are also disclosed in U.S. Pat. No. 7,264,432. This reaction platform 3 comprises flow cells 2 placed on discrete solid supports 2' and positioned on at least one essentially horizontal table 4 having lengthwise dimension X and a width dimension Y. This platform 3 includes at least one rail 5 extending parallel to the X direction and at least one displacement unit 6 having a carrying device 9, which is movable together with this displacement unit along the rail 5, for transferring objects in the X direction. The carrying device 9 is implemented here as a carrying plate 11, which is movable along the rail 5 together with the displacement unit 6, and a motorized gripping mechanism 8 for grasping and moving each discrete support 2 toward a coupled optical characterization tool 7. Using the gripping mechanism 8, the support 2' and the flow cell 2 are pulled onto the carrying plate 11 and transferred toward an observation tool 7, namely an imaging device, in the X direction utilizing the carrying device 9.

The received discrete support 2' with the flow cell 2 is assignable to its original position on the work area 4 in accordance with the X position of carrying plate 11. This detection of the X position of the carrying plate 11 and of the movement path of the gripping mechanism 8 to grasp the object (original Y position of the object) is performed via suitable sensors (not shown) for detecting linear movements, as are known to those skilled in the art from the relevant related art. The processing of the information from these sensors, the control of the drives for the movement of the carrying plate 11 in the X direction and the gripping mechanism 8 in the Y direction, and the assignment of this information to an original X/Y position of the object is preferably performed using a suitably programmed controller implemented in a digital computer (not shown), which is also a coupled part of the system.

Since in the sequencing of unknown nucleic acids, all samples contained within the flow cells will be to some degree variable, the identification of all flow cell supports 2 of the entire platform 3 is desirable and advantageous. It may also be important to track individual sequences of a series of flow cells via software applications. The defined position and orientation of the flow cells on the reaction platform allow identification of each set of sequencing samples, and thus tracking of the samples for purposes of later cross-checking and assembly.

In specific aspects of these embodiments, the flow cell 2 and the support 2' are formed as a single, integrated construct. In a specific embodiment illustrated in FIG. 3, the system 3 further provides a characterization tool 12, such as a barcode reader. This characterization tool can read one or more identifying elements of a support 2' and determine the identity of the samples in the corresponding flow cell. This identification is preferably performed while the support 2' is pulled onto the carrying plate 11 of the carrying device 9.

Figure 4:
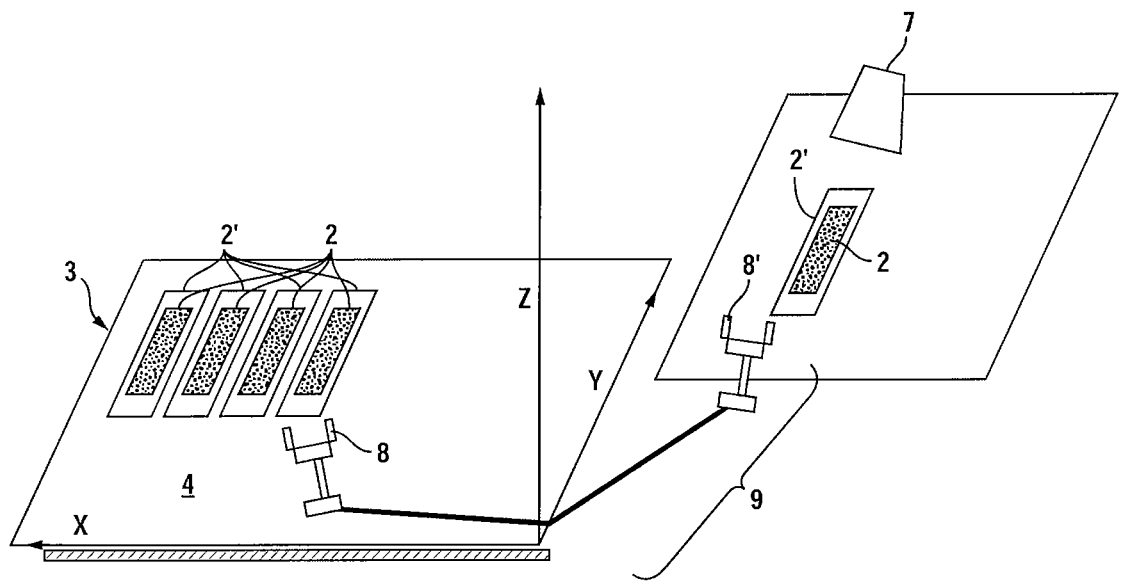
FIG. 4 is a graphic drawing illustrating a third embodiment of a system comprising a sequencing reaction platform comprising a telescopic arm and an optical imaging device.

FIG. 4 illustrates the support 2' comprising the flow cell 2 as transferred in the Z direction to an imaging system in a plane different than that of the reaction platform 3. The gripping mechanism comprising element 8 in one position and 8' in another position is implemented here as a telescopic arm; as an alternative to this, it may also be implemented as an articulated arm. The carrying device 9 is rotatable around an angle, which is preferably +180° and/or −180°, in relation to a Z axis perpendicular to the horizontal work field 4. A further alternative embodiment of the gripping mechanism (not shown) includes a rail running in the Y direction having a caterpillar tread, which may be raised and/or lowered in order to grasp and/or deposit the carrier, for example. Using this carrying device 9, the support 2' comprising the flow cell 2 may be transferred in the X direction and then deposited using the gripping mechanism 8 at a position within the viewing area of the observation tool 7, which is different from the original position of the object on the work area 4, which is significantly, the area where the chemistry is performed prior to observation. At the same time, as the gripping mechanism 8 is moved out, the identity of the samples and/or the objects is preferably detected once again and the new X/Y position of the flow cell 2 and the support 2' is stored in the coupled computer component of the system.

Figure 3:
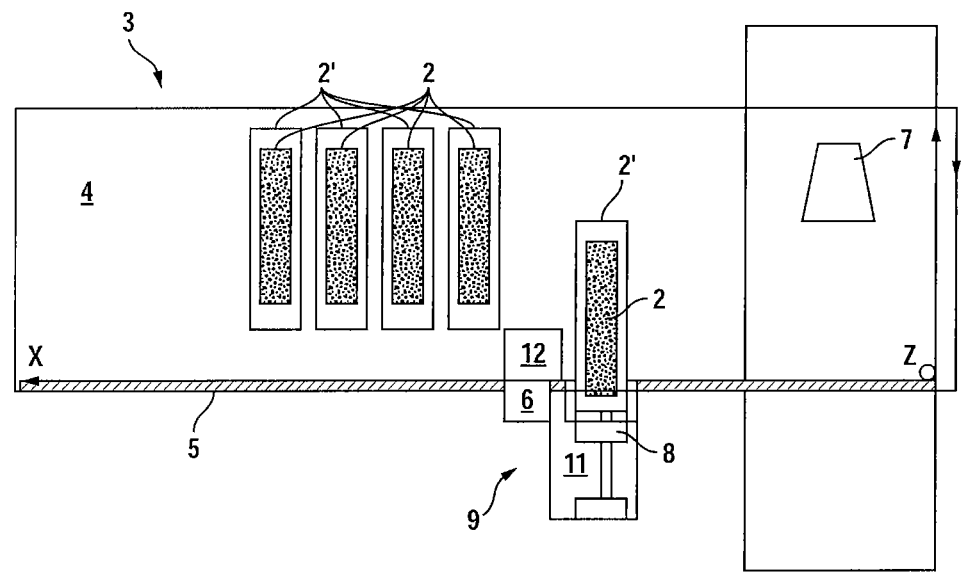
FIG. 3 is a graphic drawing illustrating a second embodiment of a system comprising a sequencing reaction platform and an optical imaging device.

From the previous description, it may be seen that the support 2' may not only be grasped, transferred in a plane, and deposited again using the gripping mechanism 8', the support 2' may also be transferred from one plane to a plane positioned above or below it in the Z direction and deposited there for further analysis using an illumination, detection and analysis component of the system of the invention. As these transfer tasks are executed, it is advantageous, but not absolutely necessary, for each of the objects to be identified or otherwise characterized using the characterization tool 12 (FIG. 3).

Figure 5:
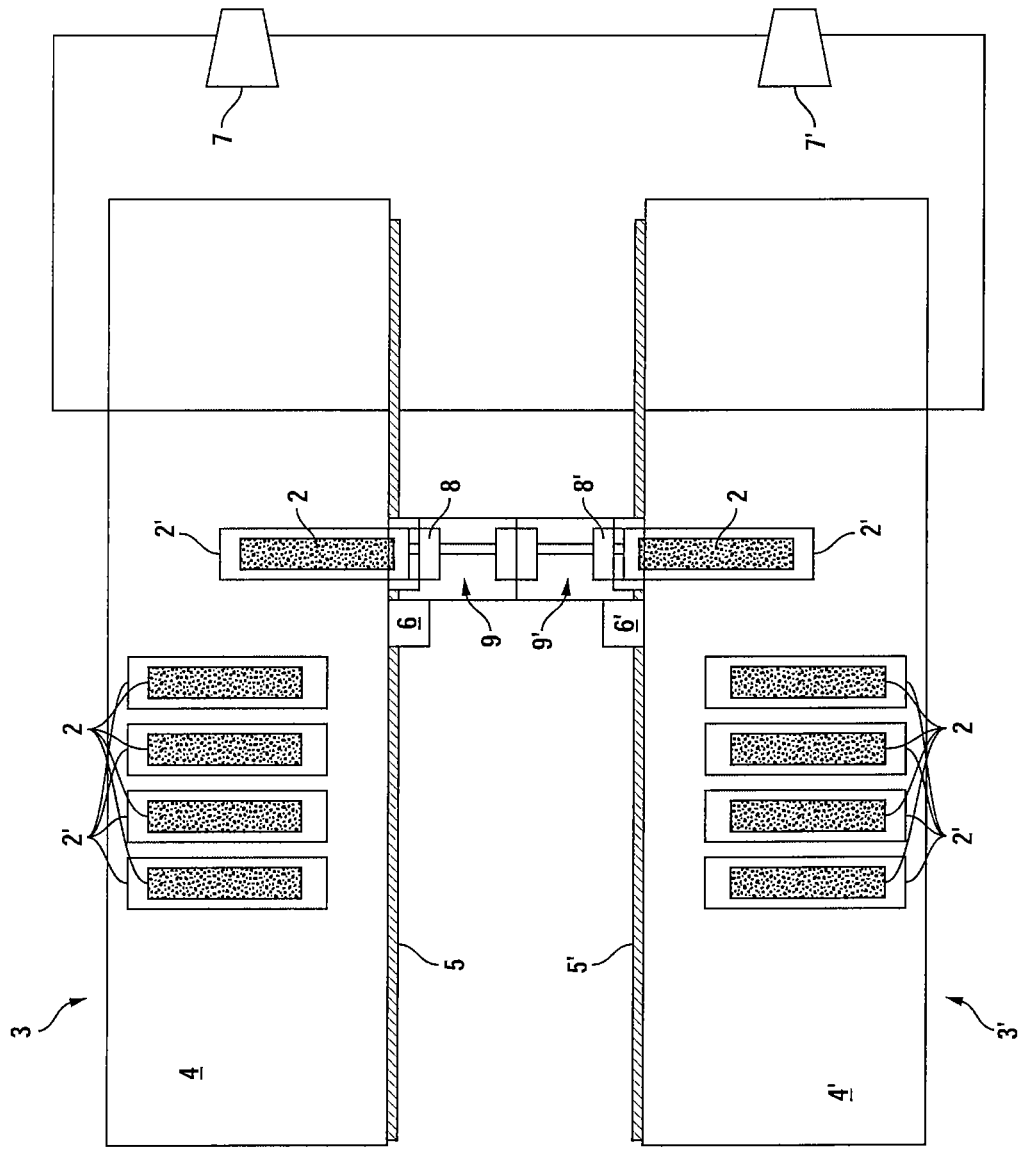
FIG. 5 is a graphic drawing illustrating a system comprising a parallel configuration of sequencing reaction platforms.

More than two work platforms may be combined into a higher-order system, as illustrated in FIG. 5. The work fields 4, 4' may be positioned parallel to one another, end-to-end in series or one over another and rotated by an arbitrary angle in a horizontal plane (not illustrated).

An aspect of the invention is timely and efficient support for the automated sequencing of reaction components. This process may involve a plurality of sequencing reactions system components that are optimized for the biochemical interrogation of nucleic acids of unknown sequence. A variety of biochemical sequencing reactions can be used with the systems of the invention, including, but not limited to, hybridization-based methods, such as disclosed in U.S. Pat. Nos. 6,864,052; 6,309,824; and 6,401,267 and U.S. patent publication 2005/0191656; sequencing by synthesis methods, such as disclosed in U.S. Pat. Nos. 6,210,891; 6,828,100; 6,833,246; 6,911,345; articles Ronaghi et al (1998), *Science*, 281:363-365; and Li et al, *Proc. Natl. Acad. Sci.*, 100:414-419 (2003); and ligation-based methods, as disclosed e.g., in International Patent applications WO1999019341, WO2005082098, WO2006073504 and article Shendure et al (2005), *Science*, 309:1728-1739.

Figure 6:
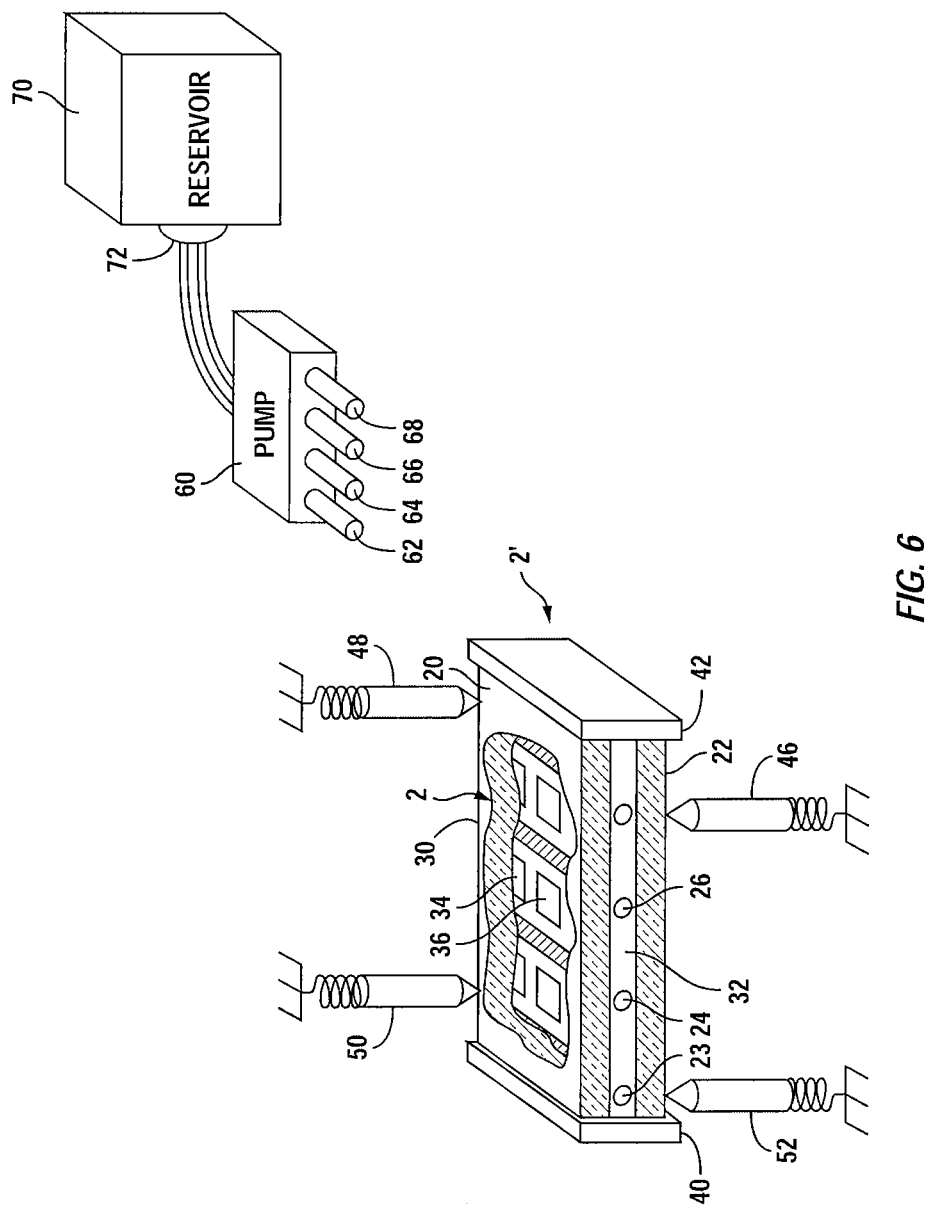
FIG. 6 is a graphic drawing illustrating a detail of a system according to the invention.

In particular embodiments, the sequencing reaction component of the system comprises one or more flow cells 2 (i.e., reaction chambers) (FIG. 6) in which the actual biochemical sequencing reaction takes place. In preferred embodiments of the invention, the flow cells 2 of the sequencing reaction component of the system comprise chambers in a support structure 2' for example constructed of optical microscope slides 20, 22 spaced by spacers 23, 24, 26, 28 into flow cell chambers 2, each with an inlet 30, an outlet 32, and a surface with exemplary regions 34, 36 that have been manufactured or otherwise treated to allow nucleic acids to be attached thereto when injected in a liquid transport through the inlet 30. The flow cell optionally includes nucleic acids or primers attached to surface regions 34, 36 of the flow cell, either as a random array or in a predetermined array of microsites so that the identity of each nucleic acid can be monitored throughout the reaction process. Nucleic acids or primers can be attached to the surface such that at least a portion of the nucleic acids or primers are individually optically resolvable when viewed through the walls of the support structure 2'.

In one preferred embodiment, the flow cells 2 comprise a substantially sealed chamber having a solid support or at least a backing on which nucleic acids of unknown sequence are immobilized. The flow cells 2 are preferably associated with a support retaining member (table or cassette) for placement of the solid support or backing in the sequencing reaction component of the system. The flow cells 2 may, for example, be arranged side-by-side, or one in front of the other on the sequencing reaction system component. Where the solid support 2' comprises is a microscope slide 22, the support retaining member will typically be of such dimensions that it may be used with slides of conventional size, (i.e., slides which typically are about 25.4 mm by 76.2 mm). Where the support is a membrane, the dimensions of the retaining member will similarly be of such dimensions that it may be used with membranes of conventional size (typically 80 mm by 120 mm), although membranes are rather more variable in size than slides.

The structural aspects of the flow cell are typically held together by an adhesive (associated with spacer elements 23, 24, 26, 28) or by a clamping means 40, 42. In certain aspects of the embodiments of the invention, the clamping means 40, 42 is capable of clamping together the portions of a plurality of flow cells. Typically, from one to around twelve or sixteen flow cells may be clamped simultaneously by a single clamping means. The flow cells can be arranged in the clamping means in a substantially horizontal or substantially vertical manner, although any position intermediate between these two positions is possible.

As an alternative or in addition to clamping, the flow cell may be provided with a biasing structure that joins the components of the flow cell. The biasing structure may comprise one or more sprung biasing members 46, 48, 50, 52. In a particular embodiment, the support is attached to a clamp by spring-loaded mounting pins, such that formation of the flow cell places the springs of the spring-loaded mounting pins under compression, which springs therefore connect the components of the flow cell.

In other specific aspects of the embodiments of the invention, the force applied to the flow cell structure by the clamping means and/or the biasing means helps to ensure a fluid-tight seal between the support and the support retaining member.

In certain aspects, it is generally preferred that the flow cell additionally comprises sealing means to assist in the formation of a substantially sealed chamber. The sealing means may be an integral part of the support retaining member, or may be provided as a separate component of the flow cell. The sealing means typically comprises a gasket, which may be made of silicon rubber or other suitable material. In one embodiment the sealing means comprises an O-ring gasket, the shape of which is generally that of a frame-like surround seated in a groove in one portion of the support retaining member. In an alternative embodiment the sealing means comprises a flattened frame-like surround gasket (about 100 to 150 µm thick). In other specific aspects, a gasket or other spacer material can be attached with an adhesive.

Either type of gasket may be discarded after a single use (if, for example, contaminated with a radioactive probe) or may be re-used if desired. The flattened gasket embodiment is particularly suitable as a disposable gasket, to be discarded after a single use. It will be apparent that the thickness of the gasket (which can be readily altered by exchanging gaskets) may, in part, determine the volume of the substantially sealed chamber.

In another aspect of the invention using small volumes in the sequencing reactions, the flow cell components are directly connected via the use of an adhesive. The adhesive is preferably introduced to a surface that provides optimal adhesion between the various flow cell components, e.g., a slide comprising an array and a coverslip.

The fluid inlet 30 allows the introduction into the substantially sealed chamber of fluids needed to process the sample on the support. Typically such fluids will be buffers, solvents (e.g. ethanol/methanol, xylene), reagents (e.g., primer- or probe-containing solutions) and the like. The fluid outlet allows for the processing fluids to be removed from the sample (e.g., for washing, or to allow the addition of a further reagent). Preferably, when the supports are being processed, their orientation is such that the fluid inlet is in the bottom portion of the substantially sealed chamber, and the fluid outlet is in the top portion of the substantially sealed chamber.

Typically, where the nucleic acid sample is supported on a slide 22, the substantially sealed chamber will have a volume of between 50 µl and 300 µl, preferably between 100-150 µl. This small volume allows for economical use of reagents and (where temperature regulation is involved) a rapid thermal response time. Where the sample is supported on a membrane, the chamber will generally be larger (up to 2-3 mls).

In particular aspects, the flow cell 2 is adapted so as to be suitable for use in performing amplification (e.g., rolling circle amplification or polymerase chain reaction amplification) on samples attached to a support. In such an embodiment, the flow cell must have an opening to allow the addition of further reagents. This opening must be designed so that it is transitory and the flow of any new liquids is very tightly controlled to prevent any leakage from the flow cell and to prevent contamination of the flow cell upon addition of any new reagents.

In a particular aspects of certain embodiments, for example those envisaged for use with PCR or other reactions in which tightly controlled temperature regulation is required, the flow cell is equipped with temperature control means to allow for rapid heating and cooling of the sample and PCR mix (i.e. thermal cycling). Typically the flow cell will be provided with an electrical heating element or a Peltier device. The flow cell may also be adapted (e.g., by provision of cooling means) to provide for improved air cooling. Temperature control in the range 3°-105° C. is sufficient for most applications.

A number of arrangements for appropriate fluid delivery means can be envisaged. In a preferred embodiment a number of reservoirs of processing fluids, (e.g., buffers, stains, etc.) are provided, each reservoir being attached to a pumping mechanism. Preferred pumping mechanisms include, but are not limited to syringe pumps 60, such as those manufactured by Hook and Tucker, (Croydon, Surrey, UK), or Kloen having a stroke volume of between 1 and 10 ml. One such pump 60 may be provided for each processing fluid reservoir, or a single pump may be provided to pump fluid from each a plurality of reservoirs, by means of a multi-port valve configuration to a plurality of syringe needles 62, 64, 66, 68 alignable with the inlets 30.

Each syringe pump 60 can in turn be attached such as by a universal connector to a central manifold 70 (such as a universal connector). Preferably the central manifold 70 feeds into a selective multi-outlet valve 72 such that, if desired, where a plurality of samples are being processed simultaneously, each sample may be treated with a different processing fluid or combination of processing fluids. A suitable selective multi-outlet valve is a rotary valve, such as the 10 outlet rotary valve supplied by Omnifit (Cambridge, UK). Thus each outlet from the multi-outlet valve 72 may be connected to a separate flow cell. One or more filters may be incorporated if desired. Typically a filter will be positioned between each reservoir and its associated syringe pump.

Each syringe pump 60 may be actuated individually by the computer control means, or two or more pumps may be actuated simultaneously to provide a mixture of two or more processing fluids. Controlling the rate of operation of each pump 60 will thus control the composition of the resulting mixture of processing fluids.

In an alternative embodiment, the fluid delivery means comprises two or more piston/HPLC-type pumps, each pump being supplied, via a multi-inlet valve, by a plurality of processing fluid reservoirs. Suitable pumps are available, for example, from Anachem (Luton, Beds, UK). The multi-inlet valve will be a rotary valve. Each pump will feed into a rotary mixer, of the type well known to those skilled in the art, thus allowing variable composition mixtures of processing fluids to be produced, if desired.

In certain aspects, the processing fluid or mixture of processing fluids is then passed through an in-line filter and then passes through a selective multi-valve outlet (such as a rotary valve) before being fed into the flow cells.

As an alternative to the generally "parallel" supply of processing fluids defined above, the processing fluids may be supplied in "series" such that, for example, fluid is passed from one substantially sealed chamber to another. This embodiment has the advantage that the amount of reagent required is minimized.

In aspects of the invention comprising one or more valves, typically the valve will be a three-way valve with two inlets, and one outlet leading to the substantially sealed flow cell. One of the valve inlets is fed, indirectly, by the reservoirs of processing fluid. The second inlet is fed by a local reservoir which, typically, will be a syringe, pipette or micro-pipette (generally 100-5000 µl volume). This local reservoir may be controlled by the computer control means or may be manually controlled. The local reservoir will typically be used where a reagent is scarce or expensive. The provision of such a local reservoir minimizes the amount of reagent required, simplifies cleaning, and provides extra flexibility in that each flow cell may be processed individually, if required.

In a specific aspect of certain embodiments of the invention, the "flow" for use in the flow cell reaction is achieved by gravity force, e.g., placement of the flow cell at an angle or by the use of an absorbent material applied on the outlet 32 of the flow cell. In other aspects of the embodiments, the flow is produced using either mechanical or electrical means, e.g., the introduction of a vacuum apparatus to the outlet edge of the flow cell. The flow cell in such embodiments may be substantially sealed, or may have both an inlet and an outlet available for transfer of fluids through the flow cell.

In another specific aspect of the embodiments of the invention, fluid enters the flow cell at the bottom, travel upwards and exits from the flow cell via the fluid outlet at the top. In a preferred aspect, however, fluid enters the flow cell from the top and is carried through the reaction via gravity, exiting the flow cell via a fluid outlet at the bottom. The fluid outlet can empty into a common collecting duct, which duct drains into a collecting vessel. The vessel is desirably removable from the apparatus to allow for periodic emptying and/or cleaning.

According to the invention, to accommodate various incompatible reaction speeds and volumes of material to be processed, the sequencing reaction component is substantially modular such that, should large numbers of flow cells and/or supported samples require processing, additional elements can be readily added to the existing equipment. In such an embodiment, the observation component as well as the sequencing reaction component of the system are preferably capable of accepting a modular array of flow cells, whether the samples are supported on slides or membranes.

The reversible integration of the sequencing reaction component to the system may include a connection to a computer control means, which can coordinate the different activities of the functional elements of the system. The computer control means can optionally control two or more of the following parameters: the selection of which pump or pumps to actuate; the absolute volume and the rate of flow of processing fluid passing through the actuated pump(s); the selection of which flow cell to feed with processing fluid; the temperature of the supported samples within the apparatus; movement of the flow cell from the sequencing reaction apparatus to the imaging component of the system; and the timing of the various events.

The invention further relates to manufacture of and use of the flow cell and/or the apparatus of the invention in processing a sample on a support, such that the invention provides: a method of processing a sample on a support using a flow cell and/or the automated sequencing reaction apparatus defined above; a method of making a flow cell; and a method of making a loosely-coupled, reversibly integrated system comprising a sequencing reaction component in accordance with the present invention.

The present invention provides a detection component for the identification of the results of the sequencing reaction component of the systems of the invention. The detection system for the signal may depend upon the labeling moiety used, which can be defined by the chemistry available. Any detection method may be used that is suitable for the type of label employed can be used in the detection component of the systems of the invention. Thus, exemplary detection methods include radioactive detection, optical absorbance detection, e.g., UV-visible absorbance detection, optical emission detection, e.g., fluorescence or chemiluminescence. Optical setups include near-field scanning microscopy, far-field confocal microscopy, wide-field epi-illumination, light scattering, dark field microscopy, photoconversion, single and/or multiphoton excitation, spectral wavelength discrimination, fluorophore identification, evanescent wave illumination, and total internal reflection fluorescence (TIRF) microscopy.

Labeled nucleic acid molecules can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091,652). Guidance can be found in the literature for applying such techniques for analyzing and detecting nanoscale structures on surfaces, as evidenced by the following references: Reimer et al, editors, *Scanning Electron Microscopy: Physics of Image Formation and Microanalysis*, $2^{nd}$ Edition (Springer, 1998); Nie et al, Anal. Chem., 78: 1528-1534 (2006); Hecht et al, *Journal Chemical Physics*, 112: 7761-7774 (2000); Zhu et al, editors, *Near-Field Optics: Principles and Applications* (World Scientific Publishing, Singapore, 1999); Drmanac, International patent publication WO 2004/076683; Lehr et al, Anal. Chem., 75: 2414-2420 (2003); Neuschafer et al, Biosensors & Bioelectronics, 18: 489-497 (2003); Neuschafer al, U.S. Pat. No. 6,289,144; and the like.

One specific imaging technique for use in the present invention is total internal reflection fluorescence (TIRF) microscopy, which can be used to visualize single fluorophores (Cy-3 or Cy-5 labeled dNTPs). TIRF microscopy uses totally internally reflected excitation light, and detection is generally carried out using evanescent wave illumination and TIRF microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. In other words, the optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths. Examples of this technique are disclosed by Neuschafer et al, U.S. Pat. No. 6,289,144; Lehr et al (cited above); and Drmanac, International patent publication WO 2004/076683.

EPI-fluorescence illumination can also be employed in the detection component of the invention. EPI-fluorescence microscopy is a technique which involves staining with a special type of histological stain called a fluorochrome which is taken up during hybridization of fluorescently labeled complementary DNA sequences.

Both TIRF and EPI illumination allow for almost any light source to be used. The light source can be rastered, spread beam, coherent, incoherent, and originate from a single or multi-spectrum source. In one specific aspect of the embodiments, imaging may be accomplished with a 100× objective using TIRF or EPI illumination and a 1.3 mega pixel Hamamatsu orca-er-ag on a Zeiss axiovert 200, or like system component.

Fluorescence resonance energy transfer (FRET) can also be used as a detection scheme. FRET in the context of sequencing is described generally in Braslavasky, et al., Proc. Nat'l Acad. Sci., 100: 3960-3964 (2003), incorporated by reference herein. Essentially, in one embodiment, a donor fluorophore is attached to the primer, polymerase, or template. Nucleotides added for incorporation into the primer comprise an acceptor fluorophore that is activated by the donor when the two are in proximity.

A suitable illumination and detection system for fluorescence-based signal is a Zeiss Axiovert 200 equipped with a TIRF slider coupled to a 80 milliwatt 532 nm solid state laser. The slider illuminates the substrate through the objective at the correct TIRF illumination angle. TIRF can also be accomplished without the use of the objective by illuminating the substrate though a prism optically coupled to the substrate. Planar wave guides can also be used to implement TIRF on the substrate.

One embodiment for the imaging system contains a 20× lens with a 1.25 mm field of view, with detection being accomplished with a 10 megapixel camera. Such a system images approx 1.5 million nucleic acid molecules attached to the patterned array at 1 micron pitch. Under this configuration there are approximately 6.4 pixels per nucleic acid molecule. The number of pixels per nucleic acid molecule can be adjusted by increasing or decreasing the field of view of the objective. For example a 1 mm field of view would yield a value of 10 pixels per nucleic acid molecule and a 2 mm field of view would yield a value of 2.5 pixels per nucleic acid molecule. The field of view may be adjusted relative to the magnification and NA of the objective to yield the lowest pixel count nucleic acid molecule that is still capable of being resolved by the optics, and image analysis software. Imaging speed may be improved by decreasing the objective magnification power, using grid patterned arrays and increasing the number of pixels of data collected in each image.

For optical signals, a combination of an optical fiber or charged couple device (CCD) can be used in the detection of the sequencing reaction. Thus, in particular embodiments, the hybridization patterns on the array formed from the sequencing reactions are scanned using a CCD camera (e.g., Model TE/CCD512SF, Princeton Instruments, Trenton, N. J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Aca. Sci. 93:4913 (1996), which allows simultaneous scanning of a very high number of labeled target nucleic acids.

In specific embodiments, the efficiency of the sequencing system can be enhanced through the use of a multi-imaging system component. For example, up to four or more cameras may be used in the imaging component of the system, preferably in the 10-16 megapixel range. Multiple band pass filters and dichroic mirrors may also be used to collect pixel data across up to four or more emission spectra. To compensate for the lower light collecting power of the decreased magnification objective, the power of the excitation light source can be increased. Throughput can be increased by using one or more flow cells with each camera, so that the imaging system is not idle while the samples are being hybridized/reacted. Because the probing of arrays can be non-sequential, more than one imaging system can be used to collect data from a set of arrays, further decreasing assay time.

One illumination schema is to share a common set of monochromatic illumination sources (about four lasers for 6-8 colors) amongst imagers. Each imager collects data at a different wavelength at any given time and the light sources would be switched to the imagers via an optical switching system. In such an embodiment, the illumination source preferably produces at least six, but more preferably eight different wavelengths. Such sources include gas lasers, multiple diode pumped solid state lasers combined through a fiber coupler, filtered Xenon Arc lamps, tunable lasers, or the more novel Spectralum Light Engine, soon to be offered by Tidal Photonics. The Spectralum Light Engine uses prism to spectrally separate light. The spectrum is projected onto a Texas Instruments Digital Light Processor, which can selectively reflect any portion of the spectrum into a fiber or optical connector. This system is capable of monitoring and calibrating the power output across individual wavelengths to keep them constant so as to automatically compensate for intensity differences as bulbs age or between bulb changes.

During the imaging process, the substrate must remain in focus. Some key factors in maintaining focus are the flatness of the substrate, orthogonality of the substrate to the focus plane, and mechanical forces on the substrate that may deform it. Substrate flatness can be well controlled, as glass plates which have better than ¼ wave flatness are readily obtained. Uneven mechanical forces on the substrate can be minimized through proper design of the hybridization chamber. Orthogonality to the focus plane can be achieved by a well adjusted, high-precision stage. After each image is acquired, it will be analyzed using a fast algorithm to determine if the image is in focus. If the image is out of focus, the auto focus system will store the position information of the out-of-focus image so that section of that array can be re-imaged during the next imaging cycle. By mapping the position at various locations on the substrate, the time required for substrate image acquisition can be reduced.

Measured signals can be analyzed manually or, preferably, by appropriate computer methods to tabulate results. The substrates and reaction conditions can include appropriate controls for verifying the integrity of hybridization and extension conditions, and for providing standard curves for quantification, if desired. For example, a control nucleic acid can be added to the sample.

In a large scale sequencing operation, each imager preferably acquires ~200,000 images per day, based on a 300 milisecond exposure time to a 16 mega pixel CCD. Thus, an instrument design for the illumination and detection component of the system of the invention may comprise four imager modules each serving four sets of quad flow cells (16 flow cells total). Each imager can include a CCD detector with 10 million pixels and be used with an exposure time of roughly 300 milliseconds. Unintentionally photo bleaching by the light source while other fluorophores are being imaged can be reduced by keeping the illumination power low and exposure times to a minimum.

By using intensified CCDs (ICCDs), data is collected of roughly the same quality with illumination intensities and exposure times that are orders of magnitude lower than standard CCDs. ICCDs are generally available in the 1-1.4 megapixel range. Because they require much shorter exposure times, a one megapixel ICCD can acquire ten or more images in the time a standard CCD acquires a single image. Used in conjunction with fast filter wheels, and a high speed flow cell stage, a one mega pixel ICCD can collect the same amount of data as a 10 megapixel standard CCD.

In a specific embodiment, electron multiplying CCD (EM-CCD) is used to image the nucleic acids. EMCCD is a quantitative digital camera technology that is capable of detecting single photon events whilst maintaining high quantum efficiency, achievable by way of a unique electron multiplying structure built into the sensor. Unlike a conventional CCD, an EMCCD is not limited by the readout noise of the output amplifier, even when operated at high readout speeds. This is achieved by adding a solid state Electron Multiplying (EM) register to the end of the normal serial register; this register allows weak signals to be multiplied before any readout noise is added by the output amplifier, hence rendering the read noise negligible. The EM register has several hundred stages that use higher than normal clock voltages. As charge is transferred through each stage the phenomenon of Impact Ionization is utilized to produce secondary electrons, and hence EM gain. When this is done over several hundred stages, the resultant gain can be (software) controlled from unity to hundreds or even thousands of times.

The EMCCD system can be used in conjunction with TIFRM technique to image multiple fluorophore labels, through integration of a multi-line laser system, preferably a solid-state laser solution with Acousto-Optical Tunable Filter (AOTF) modulation. This technique can be readily adapted for FRET analysis, preferably through integration of a suitable beam splitting device on the emission side.

A factor to be considered in high-resolution and high speed imaging and readout in connection with sequencing chemistry is the consequence vibration caused by moving parts, vibrations, which if not controlled or isolated, can disrupt image capture and result in porr image resolution. To minimize the effects of vibrations from moving parts, particularly the carrying tool 9 with the motorized gripping mechanism 8, 8' the characterization tool 7 comprising the optical components and the reaction platform 3 are specifically loosely coupled physically. In particularly, they are physically isolated from one another by shock isolators or the like, even though they are juxtaposed in operation. This requires that there be a control and sensing mechanism as part of the carrying tool 9 as well as a position registration mechanism as part of the characterization tool 7. Various such mechanisms are within the teachings of related arts. For example robotics, wherein electronic eyes, alignment marks that can be sensed and the like are used to assure transfer is accurate without inducing undue vibration into the sensitive field of view of the characterization tool so as to permit continuous or nearly continuous operation. The goal is to collect and process massive amounts of data accurately and with efficiency, while interfacing two or more technologies, involving batch-like processes with mechanical, electronic, optical and biochemical aspects, that have not heretofore been integrated into an efficient continuously operating analytic method.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured only by claims of any corresponding utility application and their equivalents. The abstract and the title are not to be construed as limiting the scope of the present invention, as their purpose is to enable the appropriate authorities, as well as the general public, to quickly determine the general nature of the invention. In the claims of any corresponding utility application, unless the term "means" is used, none of the features or elements recited therein should be construed as means-plus-function limitations pursuant to 35 U.S.C. §112, ¶6.

What is claimed is:

1. An automated assembly for sequencing nucleic acids, comprising:
    a reaction subsystem comprising one or more flow cells on a reaction platform, the one or more flow cells being configured for carrying out biochemical sequencing reactions on nucleic acid samples;
    an imaging subsystem configured for capturing optical images of a flow cell from said one or more flow cells when present in the imaging subsystem;
    a carrying device configured for transferring any of the one or more flow cells on the reaction platform to and from the imaging subsystem;
    wherein the reaction subsystem and the imaging subsystem are configured to operate independently at different rates, and
    wherein the assembly further comprises shock isolators that are constructed and arranged so as to sufficiently isolate the imaging subsystem from vibrations from the carrying device.

2. The assembly of claim 1, wherein more than one flow cells are situated on the reaction platform.

3. The assembly of claim 1, wherein the reaction subsystem comprises two or more reaction platforms.

4. The assembly of claim 1, wherein the imaging subsystem comprises a CCD (charged coupled device).

5. The assembly of claim 1, wherein the imaging subsystem is configured to detect 6 to 8 different colors.

6. The assembly of claim 1, wherein the imaging subsystem is configured so that the number of pixels per nucleic acid molecule can be adjusted by increasing or decreasing the field of view of an objective lens from 10 pixels per nucleic acid molecule to 2.5 pixels per nucleic acid molecule.

7. The assembly of claim 1, wherein the carrying device comprises a control and sensing mechanism and the imaging subsystem comprises a position registration mechanism.

8. The assembly of claim 1, wherein the imaging subsystem includes a camera having a resolution of 10 to 16 megapixels.

9. The assembly of claim 8, wherein the camera includes a CCD detector having an exposure time of about 300 milliseconds.

10. The assembly of claim 1, wherein each of the one or more flow cells comprises a sealed chamber with a volume of between 50 μL and 300 μL.

11. The assembly of claim 1, wherein the one or more flow cells on the reaction platform each contains an array of fluorescently labeled nucleic acids.

12. The assembly of claim 1, further comprising a computer programmed to coordinately control operation of the reaction subsystem, the detection subsystem, and the carrying device.

13. An automated assembly for sequencing nucleic acids, comprising:

- a reaction subsystem that is configured to support and operate a plurality of flow cells that each carry out biochemical sequencing reactions on an array of nucleic acids;
- an imaging subsystem configured for capturing optical images of the flow cells when present in the imaging subsystem;
- a carrying device configured for transferring a flow cell between the reaction subsystem and the detection subsystem; and
- shock isolators that are constructed and arranged so as to sufficiently isolate the imaging subsystem from vibrations from the reaction subsystem and from the carrying device, so that the vibrations do not disrupt image capture by the imaging subsystem.

14. The assembly of claim 13, further comprising a computer programmed to coordinately control operation of the reaction subsystem, the detection subsystem, and the carrying device.

15. The assembly of claim 13, wherein the carrying device comprises a motorized gripping mechanism.

16. The assembly of claim 13, wherein the carrying device comprises a control and sensing mechanism that regulates transfer of flow cells by the carrying device so as to prevent vibrations during transfer.

17. The assembly of claim 16, wherein the imaging subsystem comprises a position registration mechanism.

18. The assembly of claim 13, wherein the reaction subsystem comprises a number of reservoirs of processing fluids attached to a pumping mechanism.

19. The assembly of claim 13, with a plurality of flow cells on a reaction platform in the reaction subsystem, each flow cell comprising a plurality of distinguishable reaction sites.

20. The assembly of claim 19, with nucleic acids or primers attached to surface regions in the flow cells.

21. The assembly of claim 19, wherein each of the flow cells contains a sealed chamber with a volume of between 50 µL and 300 µL.

* * * * *